US006459016B1

(12) United States Patent
Rosenfeld et al.

(10) Patent No.: US 6,459,016 B1
(45) Date of Patent: Oct. 1, 2002

(54) ABSORBENT ARTICLE WITH MULTIPLE HIGH ABSORBENCY ZONES

(75) Inventors: Leonard G. Rosenfeld, East Windsor; Carlos Linares, Mountainside, both of NJ (US); Ricardo DeOliveira, New Hope, PA (US); Theresa Wysocki, Flemington, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/471,934

(22) Filed: Dec. 23, 1999

(51) Int. Cl.[7] ................................................ A61F 13/15
(52) U.S. Cl. ...................... 604/378; 604/367; 604/368; 604/374; 604/375; 428/221
(58) Field of Search .................... 604/379, 380, 604/367, 378, 368, 382, 385.01, 374, 375; 442/375, 381, 393; 428/221, 98

(56) References Cited

U.S. PATENT DOCUMENTS

| 4,537,590 A | 8/1985 | Pieniak et al. |
| 4,724,114 A | 2/1988 | McFarland et al. |
| 5,013,309 A | 5/1991 | Baigas, Jr. et al. |
| 5,248,524 A | 9/1993 | Soderlund |
| 5,599,336 A | 2/1997 | Plischke |
| 5,614,147 A | 3/1997 | Pelley |
| 5,750,066 A | 5/1998 | Vonderhaar et al. |
| 5,821,179 A | * 10/1998 | Masaki et al. .............. 442/375 |
| 5,941,863 A | * 8/1999 | Guidotti et al. ............. 604/378 |

FOREIGN PATENT DOCUMENTS

| EP | 0 401 189 A1 | 12/1990 |
| EP | 0 478 011 A2 | 4/1992 |
| EP | 0 719 531 A1 | 7/1996 |
| GB | 2 145 661 A | 4/1985 |
| GB | 2 286 832 A | 8/1995 |

* cited by examiner

Primary Examiner—John G. Weiss
Assistant Examiner—Jacqueline F Stephens
(74) Attorney, Agent, or Firm—James P. Barr

(57) ABSTRACT

An absorbent structure having an absorbent element with an upper surface and a lower surface defining between therebetween a thickness. The absorbent element has an integral structure and includes a first high absorbency zone separated from a second high absorbency zone by a portion of the thickness of the absorbent element. The high absorbency zones have absorbent fibers and superabsorbent polymer particles. The portion of the absorbent element thickness separating the first and second high absorbency zones is substantially free of superabsorbent polymer particles.

22 Claims, 8 Drawing Sheets

ABSORBENT ARTICLE WITH MULTIPLE HIGH ABSORBENCY ZONES

FIELD OF THE INVENTION

The present invention relates to a novel absorbent article such as a sanitary napkin having an absorbent structure which is characterized by having multiple integral high absorbency zones disposed within its thickness.

BACKGROUND OF THE INVENTION

Absorbent structures are known for inclusion in disposable absorbent articles used for absorbing body fluids and other exudates. Such absorbent structures have traditionally been made from readily available and relatively inexpensive materials such as cotton fibers, wood pulp fluff, cellulosic tissue or wadding, or other absorbent fibers. These materials have provided satisfactory absorbency of fluids both in terms of absorbency rate and overall absorbent capacity. Unfortunately, absorbent structures made from such materials may tend to collapse when wetted, thereby losing some of their void volume. Such structures may also allow absorbed fluid to be squeezed back out of the structure onto the user of the absorbent article. Furthermore, when such structures have absorbed fluid, they may present an uncomfortable wet feeling against the skin of the user.

More recently, superabsorbent polymer particles have been combined with the more traditional absorbent materials to provide structures with enhanced absorbency and retention, which may help to eliminate the above problems. Replacement of traditional absorbent materials with superabsorbent polymer particles may also allow for absorbent products to be thinner while retaining the absorbent capacity of thicker, bulkier products. A drawback to superabsorbent polymer particles, however, is their relatively high cost compared to the more traditional absorbent materials.

Additionally, since superabsorbent polymer particles tend to swell as they absorb fluid, they may cause what is commonly known as gel-blocking. In other words, as fluid is absorbed by the particles of superabsorbent polymer, those particles swell and may form an occlusive layer of swollen superabsorbent particles. This occlusive layer then prevents the passage of additional fluid into the structure. Thus, the superabsorbent polymer particles must be properly placed within an absorbent structure to allow for this swelling and to most fully utilize their absorbent capacity. Generally, prevention of gel-blocking has been realized by mixing superabsorbent polymer particles with spacer materials, such as absorbent or nonabsorbent fibers, or by placing the superabsorbent polymer particles toward the bottom of the absorbent structure. However, although these methods of superabsorbent polymer placement may minimize gel-blocking, they do not effect the most efficient use of the superabsorbent polymer's absorbent capacity.

Therefore, what is needed is an absorbent structure with good absorbency and retention of fluid. What is also needed is an absorbent structure that helps to provide a dry feel to the skin of a user when used in an absorbent article. What is further needed is an absorbent structure with superabsorbent polymer particles spaced and placed within the structure to most fully utilize the absorbency and retention capabilities of the superabsorbent polymer particles.

SUMMARY OF THE INVENTION

It is an object of the present invention to provide an absorbent article with good absorbency and retention of fluid that will help to provide a dry feel to the skin of a user of the article.

It is another object of the present invention to provide an absorbent structure with superabsorbent polymer particles spaced and placed within the structure to most fully utilize the absorbency and retention capabilities of the superabsorbent polymer particles.

In accordance with the present invention, there has been provided a novel absorbent structure for use in absorbent articles. The absorbent structure includes an absorbent element having an integral structure formed from absorbent fibers and super absorbent particles. The absorbent structure may optionally include additional laminate layers such as one or more layers of tissue and/or a nonwoven fabric. The nonwoven fabric may have a lower density and a higher porosity than the absorbent element of the invention to allow for rapid fluid acquisition and the subsequent transfer of the acquired fluid to an adjacent, slower absorbing, higher density absorbent element. Alternatively, the nonwoven fabric may have a higher density and a lower porosity than the absorbent element to increase fluid wicking throughout the nonwoven fabric. Preferably, lower-density nonwoven fabrics are placed adjacent the body-facing surface of an absorbent element, and higher-density nonwoven fabrics are placed adjacent the garment-facing surface of an absorbent element.

The absorbent structure of the invention has peripheral edges and a center region. The center region is that portion of the structure which is inward from the peripheral edges of the structure and which is intended to accept incoming fluid when the structure is used in an absorbent article. The absorbent element also has peripheral edges and a center region (as described above). The peripheral edges of the absorbent element may be coterminous with the peripheral edges of the absorbent structure or may be inward from or extend beyond the peripheral edges of the absorbent structure.

The absorbent element has an upper surface and a lower surface defining therebetween an absorbent element thickness. The absorbent element further has an integral structure and further includes a first high absorbency zone and a second high absorbency zone separated from one another by a portion of the element thickness. Each of the first and second high absorbency zones comprises an integral mixture of absorbent fibers and superabsorbent polymer particles and has a first surface and a second surface. As used herein, the terminology "integral" means a unitary structure wherein the absorbent fibers are intermeshed throughout the entire absorbent element. Thus, there are no identifiable laminate layers which are separable from other layers within the element. Consequently, the surfaces of the high absorbency zones are not, per se, identifiable surfaces. As used herein, the terminology "surface" as it relates to each of the high absorbency zones represents the location at which a transition occurs from a section of the integral structure substantially free of superabsorbent polymer particles to a section of the integral structure containing a mixture of absorbent fibers and superabsorbent polymer particles.

The first surface of the first high absorbency zone may optionally be coplanar with the upper surface of the absorbent element, or alternatively, the first high absorbency zone may be below or spaced from the upper surface of the absorbent element wherein the upper surface is substantially free of superabsorbent polymer particles and contains only absorbent fibers. Subjacent to the first high absorbency zone is a second high absorbency zone, each zone having a respective thickness. The thickness of the first high absorbency zone may be the same as or different from the thickness of the second high absorbency zone. Preferably, the thickness of each of the first and second high absorbency zones comprises less than about 35% of the thickness of the absorbent element. More preferably, the thickness of each of the first and second high absorbency zones comprises less than 20% of the thickness of the absorbent element. The first high absorbency zone is separated from the second high absorbency zone by a portion of the absorbent element thickness which is substantially free of superabsorbent particles. Additionally, the portions of the absorbent element that are outside of the first and second high absorbency zones are substantially free of superabsorbent polymer particles.

The superabsorbent polymer particles are mixed with absorbent fibers within the first and second high absorbency zones. In a preferred embodiment, the superabsorbent polymer particles are uniformly and homogeneously mixed with the absorbent fibers within the first and second high absorbency. Alternatively, the superabsorbent particles may be distributed within one or both of the first and second high absorbency zones on an increasing gradient wherein the concentration of superabsorbent particles increases from a minimum at the first surface of the high absorbency zone to a maximum at the second surface of the high absorbency zone, or a decreasing gradient, wherein the concentration of superabsorbent particles decreases from a maximum at the first surface of the high absorbency zone to a minimum at the second surface of the high absorbency zone. Alternatively, the superabsorbent particles can be distributed in a manner such that a maximum concentration of these particles occurs in a region centered at approximately half the distance between the first surface and the second surface of one or both of the high absorbency zones.

In a most preferred embodiment the upper surface of the absorbent element is substantially free of superabsorbent particles, the first high absorbency zone being slightly below the upper surface of the absorbent element wherein the upper surface of the absorbent element comprises 100% absorbent pulp fibers.

In accordance with the present invention, there has been provided an absorbent structure utilized in absorbent articles such as sanitary napkins, diapers, incontinence articles and the like. An embodiment of such an article comprises the absorbent element of the invention contained between a liquid-permeable body-facing layer and a liquid-impermeable barrier layer and positioned such that the body-facing layer is adjacent the upper surface of the absorbent element and the impermeable barrier layer is adjacent the lower surface of the absorbent element.

Also provided in accordance with the present invention is a novel apparatus for intermittently applying a particulate material to a substrate, the apparatus comprising two applicator valve assemblies, each applicator valve assembly comprising a stationary funnel having an opening and positioned within a moveable housing such that the moveable housing is free to move relative to the stationary funnel, the moveable housing comprising at least one slot opening and at least one recycle hole spaced from the slot opening, wherein the moveable housing moves relative to the stationary funnel to provide an application phase to allow passage of particulate material by free-fall through the stationary funnel opening and the slot opening when the stationary funnel opening aligns with the slot opening, and a recycle phase to prevent dispensing of particulate material onto the substrate when the stationary funnel opening aligns with the at least one recycle hole.

Also provided in accordance with the present invention is a novel method for intermittently applying particulate material to a substrate comprising the steps of:

providing a substrate;

providing a continuous supply of first particulate material from a first supply source to a first valve having a powder application phase and a recycle phase;

disposing the first valve to the powder application phase to allow passage of first particulate material by free-fall therethrough;

dispensing the first particulate material through the first valve onto at least a portion of a surface of the substrate;

disposing the first valve to the recycle phase to prevent dispensing of first particulate material onto the substrate and to retain the first particulate material within the first valve;

conveying the first particulate material back to the first supply source;

providing a continuous supply of particulate material from a second supply source to a second valve having a powder application phase and a recycle phase;

disposing the second valve to the powder application phase to allow passage of second particulate material by free-fall therethrough;

dispensing the second particulate material through the second valve onto at least a portion of a surface of the substrate;

disposing the second valve to the recycle phase to prevent dispensing of second particulate material onto the substrate and to retain the second particulate material within the second valve; and conveying the second particulate material back to the second supply source.

DETAILED DESCRIPTION OF THE INVENTION

Further characteristics and advantages of the invention will become clear from the following detailed description, appended drawings, and non-limiting examples.

The present invention is directed to novel absorbent articles such as, for example, sanitary napkins, having a central absorbent structure adapted to receive and retain body exudates. More particularly, the absorbent articles of the present invention have a novel absorbent structure which includes an absorbent element having an integral structure formed from a combination of absorbent fibers and super absorbent particles and further including a first high absorbency zone located adjacent an upper surface of the absorbent element and a second high absorbency zone spaced below and vertically separated from the first high absorbency zone by a portion of the absorbent element thickness. The absorbent articles will generally have a body facing, liquid-permeable cover layer, a garment-facing, liquid-impermeable barrier layer, and an absorbent structure between the body-facing layer and the barrier layer. The absorbent structure may optionally include a multi-layer laminate structure having one or more layers of nonwoven fabrics and/or tissue in addition to the absorbent element. In a preferred embodiment, the absorbent structure comprises an upper, body facing fluid transfer layer formed from a nonwoven fabric and an underlying absorbent element between the fluid transfer layer and the barrier layer. The fluid transfer layer preferably has a porosity that is greater than the porosity of the absorbent element.

The absorbent element has a center region and peripheral edges, and an upper surface and a lower surface defining therebetween an absorbent element thickness. The absorbent element has a first high absorbency zone having a first high absorbency zone first surface and a first high absorbency zone second surface separated by a first high absorbency zone thickness (hereinafter "first zone thickness"), and a second high absorbency zone having a second high absorbency zone first surface and a second high absorbency zone second surface separated by a second high absorbency zone thickness (hereinafter "second zone thickness"). The first high absorbency zone first surface may optionally be coplanar with the upper surface of the absorbent element or alternatively it may be slightly below the upper surface wherein the region between the upper surface and the first high absorbency zone first surface is substantially free of superabsorbent particles. The second high absorbency zone is spaced below the first high absorbency zone such that the first high absorbency zone second surface is separated from the second high absorbency zone first surface by a portion of the absorbent element thickness which is substantially free of superabsorbent particles.

The novel absorbent structure of the present invention is intended for use in disposable absorbent articles. These articles are adapted to be placed in a crotch portion of an undergarment and worn by the user in direct contact with the body for the purpose of absorbing body fluids and are subsequently thrown away after a single use.

Figure 1:
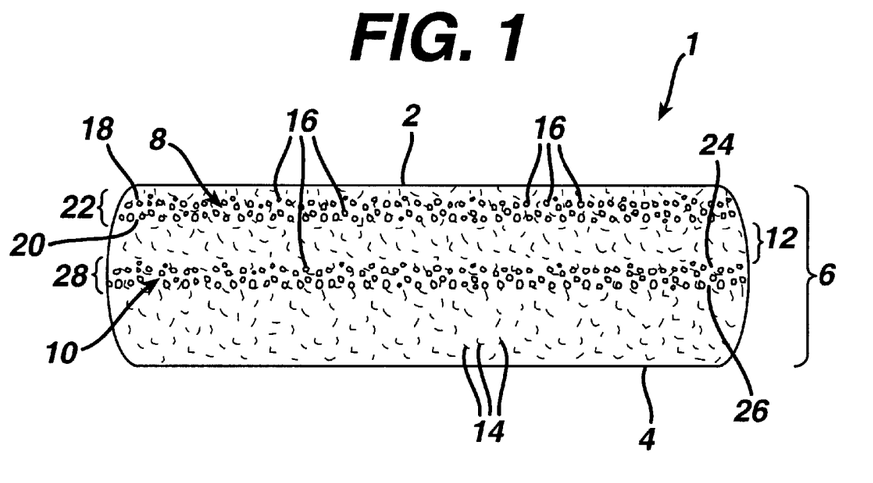
FIG. 1 is a sectional view of a first preferred embodiment of the absorbent element of the invention.

Referring to FIG. 1, there is shown a sectional view of a first preferred embodiment of the absorbent element 1 of the present invention. FIG. 1 shows an integral absorbent element 1 with an upper surface 2 and a lower surface 4 defining therebetween an absorbent element thickness 6. The absorbent element further has a first high absorbency zone 8 and a second high absorbency zone 10 separated from one another by a portion 12 of the absorbent element thickness. Both the first high absorbency zone and the second high absorbency zone comprise a mixture of absorbent fibers 14 and superabsorbent polymer particles 16. The superabsorbent polymer particles are substantially contained within the first and second high absorbency zones, and the portion 12 of the absorbent element thickness separating the first and second high absorbency zones is substantially free of superabsorbent polymer particles. It can be seen in a preferred embodiment illustrated by FIG. 1 that an upper surface 2 is substantially free of superabsorbent polymer particles 16, and that the superabsorbent polymer particles 16 are separated from one another by absorbent fibers 14 within the first and second high absorbency zones 8, 10.

The first high absorbency zone has a first high absorbency zone first surface 18 and a first high absorbency zone second surface 20 defining therebetween a first high absorbency zone thickness 22. The second high absorbency zone has a second high absorbency zone first surface 24 and a second high absorbency zone second surface 26 defining therebetween a second high absorbency zone thickness 28. Each of the first high absorbency zone thickness 22 and the second high absorbency zone thickness 28 preferably comprises less than 35% of the absorbent element thickness 6. The first high absorbency zone thickness 22 may be the same as or different from the second high absorbency zone thickness 28.

The absorbent fibers of the present absorbent element may comprise any absorbent fiber known in the art, including without limitation, naturally occurring fibers or synthetic fibers. Examples of naturally occurring absorbent fibers are wood pulp, cotton, silk, hemp and the like, while examples of synthetic absorbent fibers include without limitation rayon fibers, individualized cross-linked cellulose fibers, acrylic fibers, and the like. A preferred absorbent fiber for the absorbent element of the invention is wood pulp fluff.

For the purposes of the present invention, the term "superabsorbent polymer" refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Suitable superabsorbent polymer particles for use in the present invention are crosslinked polyacrylates, such as the product offered by Sumitomo Seika Chemicals Co., Ltd. Of Osaka, Japan, under the designations of J550™, SA60N Type II™, SA60SL™, and SA60SX™, and the products offered by Chemdal International, Inc. of Palatine, Ill., under the designations of Chemdal 1000™, 2000™, 2100™, 2100A™, and 2300™. Suitable superabsorbent fibers are manufactured by Oasis Inc. and Camelot Inc.

Although a wide range of superabsorbent polymer particles would work in this invention, preferred superabsorbent particles are those that are well suited to being mixed at concentrations by weight of 30% or more with pulp fibers without exhibiting gel-blocking. In accordance with the present invention, each high absorbency zone may contain between 10% and 80% by weight of superabsorbent particles. It is not necessary that the first and second high absorbency zones contain the same percentage or even the same type of superabsorbent polymer particles. In some cases, it may be preferable for the first high absorbency zone to contain a smaller percentage of superabsorbent particles of a first type, and for the second high absorbency zone to contain a higher percentage of superabsorbent particles of a second type. In the preferred embodiment of the invention the superabsorbent particles are present in each high absorbency zone at a loading of between 30 and 55 grams per square meter.

The absorbent element according to the present invention may also comprise other absorbent or nonabsorbent materials, such as binders, nonabsorbent fibers, odor controlling particles, or perfumes. Examples of suitable binder materials include without limitation, ethylene vinyl acetate based latex binders, adhesives, and thermally fusible fibers, such as bicomponent fibers. Examples of suitable nonabsorbent fibers include without limitation, polyester fibers, polyolefin fibers, and bicomponent fibers.

Absorbent elements according to the present invention are commonly formed by air-laying the fibers and superabsorbent polymer particles. A preferred method of forming the absorbent element of the invention involves first forming pulp fluff from a pulp board in a hammer mill or similar equipment designed to fiberize or separate and "open" the pulp fibers in the board. The separated pulp fibers are then entrained in an air stream and deposited on a foraminous surface to form a pulp batt or pad. The pulp batt or pad thus formed is a collection of individual fibers in a very loose configuration. The fibrous batt is substantially uncompressed, leaving spaces between the fibers that comprise the batt. Superabsorbent polymer particles that are added to the loose batt fall into these spaces between the fibers. The superabsorbent polymer particles may be added to a portion of the air-entrained fibers for deposition substantially throughout the thickness of a first or a second high absorbency zone. Alternatively, the superabsorbent polymer particles may be deposited directly onto a formed pulp batt at the desired points in the pulp deposition process to ensure that the superabsorbent particles are located at the desired zones within the thickness of the structure. In the former case, the particles are mixed with pulp fibers throughout the high absorbency zones of the integral absorbent structure. In the latter case, the particles fall into the spaces between the absorbent fibers to form fairly concentrated high absorbency zones within the integral absorbent structure with absorbent fibers separating the particles in each zone. In either case, the particles within each zone are separated from one another by fibers. In a preferred embodiment, absorbent fibers are laid over the top of the first high absorbency zone so that the upper surface of the absorbent element is substantially free of superabsorbent polymer particles. In all cases, however, the superabsorbent polymer particles are substantially separated from one another by intermeshed pulp fibers within the first and second high absorbency zones to maintain the integral structure of the absorbent element.

The first high absorbency zone located adjacent the upper surface of the absorbent element may extend across the entire upper surface 2 of absorbent element 1 or alternatively, may be confined to one or more particular localized regions of the absorbent element, such as for example, being located solely in a central region and spaced inwardly away from the peripheral edges of the absorbent element. Likewise, the second high absorbency zone may extend from one peripheral edge to an opposite peripheral edge of the absorbent. Alternatively, the second high absorbency zone may be confined to one or more particular localized regions of the absorbent element, such as, for example, being located solely in a central region and spaced inwardly from the peripheral edges of the absorbent element, or being located only along one or more of the peripheral edges of the absorbent element. In further embodiments, one or both of the first and second high absorbency zones may comprise multiple discrete regions substantially separated from one another.

The thickness of the absorbent structure may be uniform throughout the expanse of the absorbent element or, for the purpose of specific fit, flexibility and absorbency requirements, the absorbent structure may have a tapered profile wherein certain areas of the structure, such as a central region, are thicker than other areas.

Figure 2:
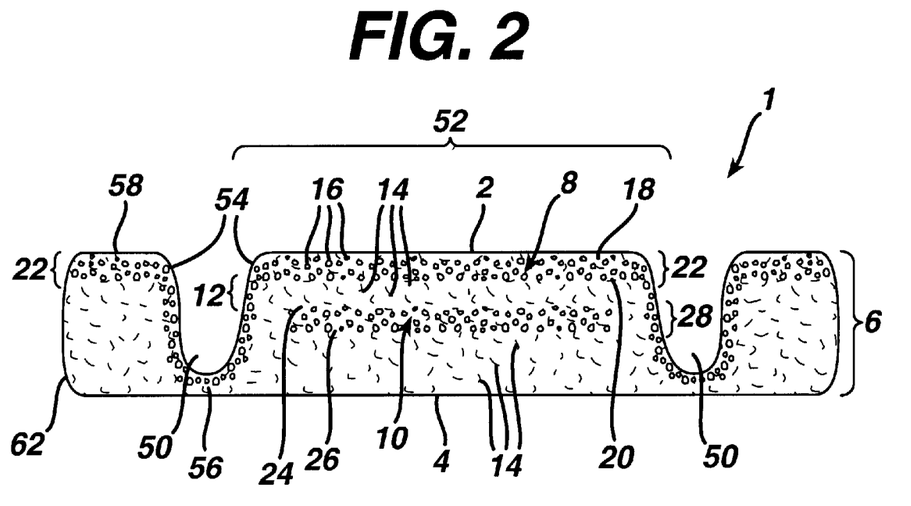
FIG. 2 is a sectional view of a second preferred embodiment of the absorbent element of the invention.

As shown in FIG. 2, the second high absorbency zone may be surrounded by boundaries, such as densified channels 50. In this embodiment, the first high absorbency zone 8 is coextensive with the absorbent element upper surface 2. The second high absorbency zone 10 is completely contained in a centrally located region 52 between the channels 50. The boundaries may also comprise other structural elements, such as raised areas measuring a greater thickness or caliper than the surrounding areas; repellent-treated areas; embossed or depressed areas measuring a lesser caliper or thickness than the surrounding areas; colored areas having inks or other coloring agents printed thereon or being otherwise treated to exhibit a color that is visually perceptible as different from the color of the surrounding areas or the edges of the absorbent structure. Alternatively, the top surface of the absorbent structure may be partially covered by a film or other impermeable material, leaving only a central opening uncovered.

An important feature of the present invention is that the entire absorbent element, including the first and second high absorbency zones, be an integral structure, wherein the absorbent fibers that comprise the absorbent element are continuously intermingled with the absorbent fibers that comprise the first and second high absorbency zones, and no discernible laminate or separate structure is present. In other words, the superabsorbent-containing first and second high absorbency zones are not formed as nor are they present as separable layers within the absorbent element; rather, they are simply regions of varying absorbency within the absorbent element. An advantage of this integral type of structure is that it remains a single whole structure during the absorption of fluid, and consequently, it is not subject to delamination or gapping as fluid is absorbed. Such gapping or delamination disrupts the fluid transport and distribution capabilities of the structure and may diminish its overall absorbency. An integral absorbent structure also allows for a simpler process of absorbent article construction.

The absorbent element shown in FIG. 2 is an alternative embodiment of the present invention. FIG. 2 shows an integral absorbent element 1 with an upper surface 2 and a lower surface 4 defining therebetween an absorbent element thickness 6. The absorbent element further has a first high absorbency zone 8 and a second high absorbency zone 10 separated from one another by a portion 12 of the absorbent element thickness. Both the first high absorbency zone and the second high absorbency zone comprise absorbent fibers 14 and superabsorbent polymer particles 16. The superabsorbent polymer particles are substantially contained within the first and second high absorbency zones, and the portion 12 of the absorbent element thickness separating the first and second high absorbency zones is substantially free of superabsorbent polymer particles. It can be seen in the embodiment illustrated by FIG. 2 that the upper surface 2 is substantially free of superabsorbent polymer particles 16, and that the superabsorbent polymer particles 16 are separated from one another by absorbent fibers 14 in the first and second high absorbency zones 8, 10.

The first high absorbency zone has a first high absorbency zone first surface 18 and a first high absorbency zone second surface 20 defining therebetween a first high absorbency zone thickness 22. The second high absorbency zone has a second high absorbency zone first surface 24 and a second high absorbency zone second surface 26 defining therebetween a second high absorbency zone thickness 28. Each of the first high absorbency zone thickness 22 and the second high absorbency zone thickness 28 preferably comprises less than 35% of the absorbent element thickness 6. The first high absorbency zone thickness 22 may be the same as or different from the second high absorbency zone thickness 28.

FIG. 2 also shows the presence of two densified channels 50, which may be compressed into the absorbent element after its formation. The channels define centrally located region 52 therebetween. Each channel 50 has inner edges 54 and a lowermost portion or bottom 56. Each channel defines a side portion 58 of the element which includes the portion of the element that is outboard of the channel 50, that is, that portion of the article that is between the channel 50 and the outside edge 62 of the element. These side portions 58 may contain superabsorbent or they may be free of superabsorbent. In the preferred embodiment shown in FIG. 2, the first high absorbency zone extends into the side portions 58, but the second high absorbency zone is confined to the centrally located region 52 between the channels 50.

Figure 3:
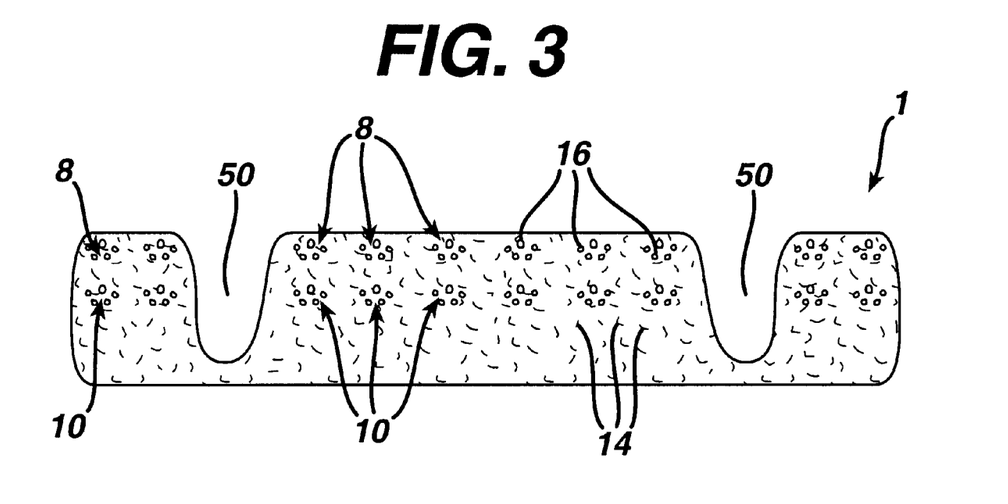
FIG. 3 is a sectional view of a third preferred embodiment of the absorbent element of the invention.

Neither the first nor the second high absorbency zone needs to be continuous. As shown in FIG. 3, absorbent element 1 contains absorbent fibers 14, super absorbent particles 16 and two densified channels 50, the first high absorbency zone 8 and the second high absorbency zone 10 may both have discontinuous regions. This type of configuration may be preferred in some cases to prevent gel-blocking and to allow fluid to pass quickly into the absorbent element when the fluid first enters the absorbent element.

Figure 4:
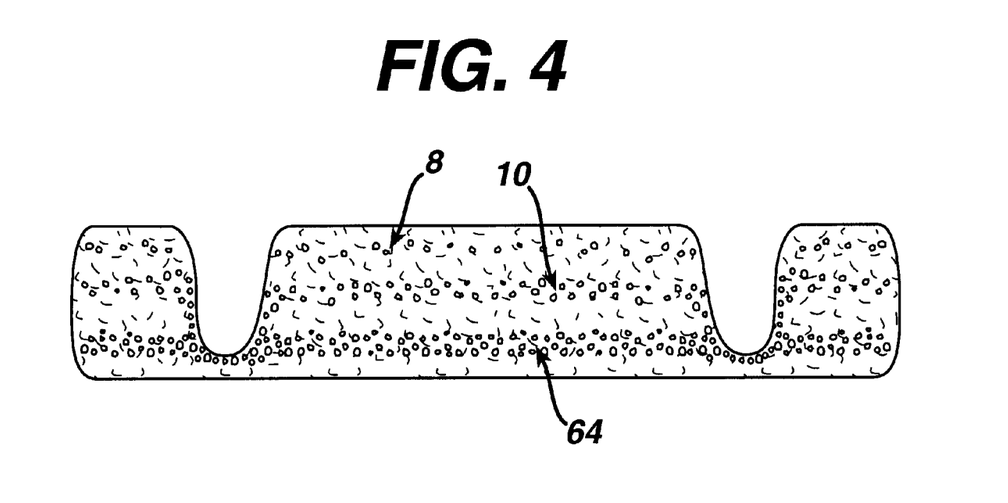
FIG. 4 is a sectional view of a fourth preferred embodiment of the absorbent element of the invention.

The number of high absorbency zones within the absorbent element of the invention need not be limited to two. Accordingly, three or more high absorbency zones may be present throughout the thickness of the absorbent element. The sectional view of the embodiment of the absorbent element shown in FIG. 4 has three high absorbency zones all separated from one another by a portion of the thickness of the absorbent element. In the embodiment of FIG. 4, a first high absorbency zone 8 contains a smaller percentage of superabsorbent particles than a second high absorbency zone 10, which contains a smaller percentage of superabsorbent particles than a third high absorbency zone 64. This arrangement may be desirable to minimize gel-blocking and to allow most of the absorbed fluid to be retained further from the upper surface of the absorbent element.

Figure 5:
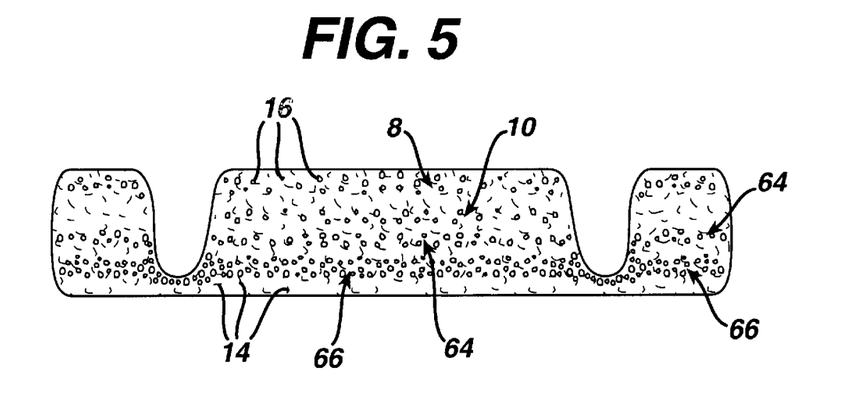
FIG. 5 is a sectional view of a fifth preferred embodiment of the absorbent element of the invention.

The sectional view of the embodiment shown in FIG. 5 shows four high absorbency zones with the first high absorbency zone 8, the third high absorbency zone 64, and fourth high absorbency zone 66 extending nearly to the peripheral edges of the absorbent element. The second high absorbency zone 10 in FIG. 5 is substantially confined to the center of the absorbent element. This configuration may be desirable in applications where more absorbency is required in the center of the article.

Figure 6:
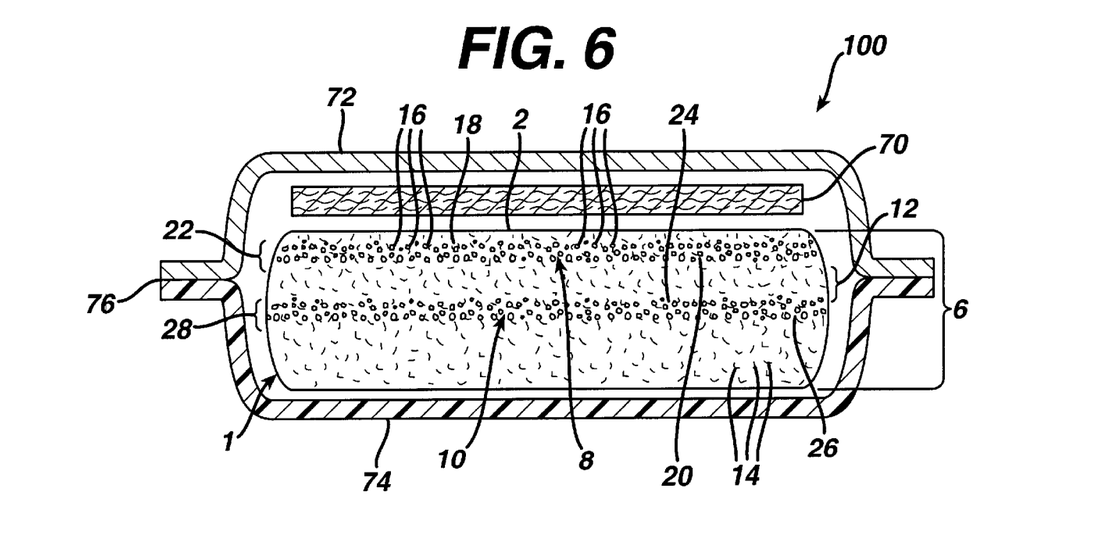
FIG. 6 is a sectional view of a first preferred embodiment of the absorbent article of the invention.

The absorbent article 100 shown in FIG. 6 is a sectional view of a first preferred embodiment of the absorbent article of the present invention. The absorbent article 100 of FIG. 6 has an integral absorbent element 1 comprising a first high absorbency zone 8 and a second high absorbency zone 10 separated from one another by a portion 12 of the absorbent element thickness. The first high absorbency zone has a first high absorbency zone first surface 18 and a first high absorbency zone second surface 20 defining therebetween a first high absorbency zone thickness 22. The second high absorbency zone 10 has a second high absorbency zone first surface 24 and a second high absorbency zone second surface 26 defining therebetween a second high absorbency zone thickness 28. As discussed above, the first and second high absorbency zones are integrally formed with the absorbent element and thus the first surfaces 18, 24 and the second surfaces 20, 26 are not, per se, identifiable surfaces. Rather, they are marked by an absence of any superabsorbent polymer particles. The absorbent element 1 comprises absorbent fibers 14 and superabsorbent polymer particles 16. The superabsorbent polymer particles 16 are substantially contained within the first high absorbency zone thickness 22 and the second high absorbency zone thickness 28. It can be seen in the preferred embodiment illustrated by FIG. 6 that the upper surface 2 is substantially free of superabsorbent polymer particles 16, and that the superabsorbent polymer particles 16 are mixed with absorbent fibers 14 in the first high absorbency zone thickness 22 and the second high absorbency zone thickness 28. The integral absorbent element is overlaid with a fluid transfer layer 70 and positioned between a liquid permeable, body-facing layer 72 and a liquid impermeable, barrier layer 74 such that the upper surface 2 is adjacent the fluid transfer layer 70, which is adjacent the body-facing layer 72. The body-facing layer 72 and the barrier layer 74 are joined to one another around the periphery of the absorbent element to form what is commonly known as a flange seal 76.

Figure 7:
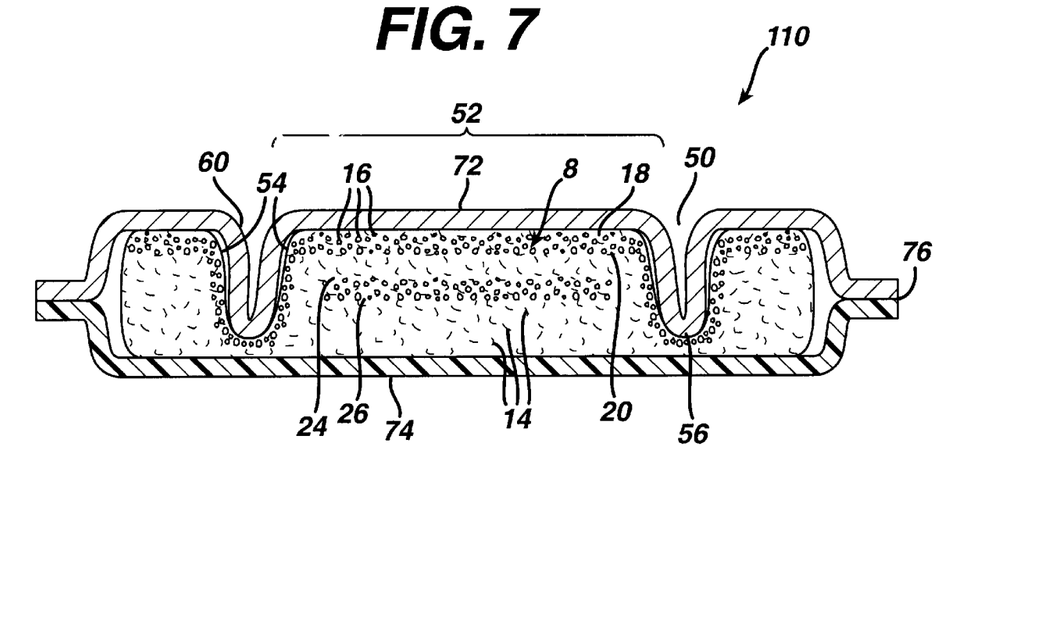
FIG. 7 is a sectional view of a second preferred embodiment of the absorbent article of the invention.

The absorbent article 110 shown in FIG. 7 is a sectional view of a second preferred embodiment of the absorbent article of the present invention. The absorbent article 110 of FIG. 7 has an integral absorbent element comprising a first high absorbency zone 8 and a second high absorbency zone 10 essentially as shown in FIG. 2 and described in detail above. As shown in FIG. 7, the integral absorbent element of FIG. 2 is positioned between a liquid permeable, body-facing facing layer 72 and a liquid impermeable, barrier layer 74 such that the absorbent element upper surface 2 is adjacent the body-facing layer 72. The body-facing layer 72 follows the shape of the upper surface to line the inner edges 54 of the channels. The body-facing layer 72 may be connected or secured to the bottom 56, or lowermost portion, of the channel 50, as shown in FIG. 7. The body-facing layer 72 and the barrier layer 74 are joined to one another around the periphery of the absorbent element to form what is commonly known as a flange seal 76.

Although the articles 100 and 110 shown in FIGS. 3 and 4 respectively have the body-facing layer 72 and the barrier layer 74 joined together by a flange seal 76, this is for illustrative purposes only. The presence of a flange seal is not necessary to achieve the benefits and advantages of the invention. Alternatively, the body-facing layer of the absorbent article may be wrapped completely around the absorbent element and overlapped and sealed to itself on the underside of the article. The barrier layer may be present either between the absorbent element and the overlapped portion of the body-facing layer, or on the outer surface of the overlapped portion of the body-facing layer. Other methods of securing a body-facing layer and a barrier layer to an absorbent article structure will be apparent to those who are familiar with the construction of absorbent articles.

The body-facing cover layer may comprise any soft, flexible, porous material which allows liquid to pass therethrough, and may, for example, be comprised of a nonwoven fibrous sheet or an apertured or perforated plastic film. Examples of suitable nonwoven fibrous sheets include without limitation, carded webs, spunbond webs, meltblown webs, random-laid webs, and the like. The fibers comprising such webs may comprise polyester, polyethylene, polypropylene, rayon, or combinations of these. The webs may further comprise bonding agents, surfactants, or other treatments. A preferred material for the body-facing layer of the invention is a homogeneous blend of high denier polypropylene staple fibers and low denier polypropylene staple fibers. The high denier staple fibers and the low denier staple fibers preferably differ by 2 denier, where the low denier staple fibers preferably have a denier of about 3 and the high denier staple fibers preferably have a denier of about 5. The high denier staple fibers are present in the non-woven fabric in an amount of from 40 to 60 weight percent. The low denier staple fibers are present in the non-woven fabric in an amount of from 40 to 60 weight percent based on the total weight of the non-woven fabric.

The barrier layer is a liquid-impermeable layer, and may comprise any flexible material that prevents the transfer of fluid but does not necessarily prevent the passages of gases. Commonly used materials are polyethylene or polypropylene films. Other suitable polymeric film materials that may be used as impermeable barriers include, but are not limited to polyesters, polyamides, polyethylene vinyl acetate, polyvinyl chloride, and polyvinylidene chloride, and the like and combinations thereof. Co-extruded and laminated combinations of the foregoing, wherein such combinations are permitted by the chemical and physical properties of the film, may be used. Fluid impermeable foams and repellent treated papers may also be used. Films that are fluid barriers, but.permit gases to transpire, i.e., "breathable films", may be used. These may be chosen from polyurethane films and from micro-porous films, where micro-porosity is created by ionizing radiation or by leaching out of soluble inclusions using aqueous or non-aqueous solvents. Fabrics whose surfaces have been made repellent or whose pores are small by virtue of close packing of fibers, or whose pores have been reduced in size by closing off large liquid admitting pores, may also be used alone, or together with breathable films, as breathable barriers.

A suitable backing sheet material can be an opaque polyolefin, e.g., polyethylene, web impermeable to body fluids and about 0.001 inch thick. Another suitable sheet material for this purpose is a polyester, e.g., polyethylene terephthalate, web having a thickness of about 0.0005 inch.

Figure 8:
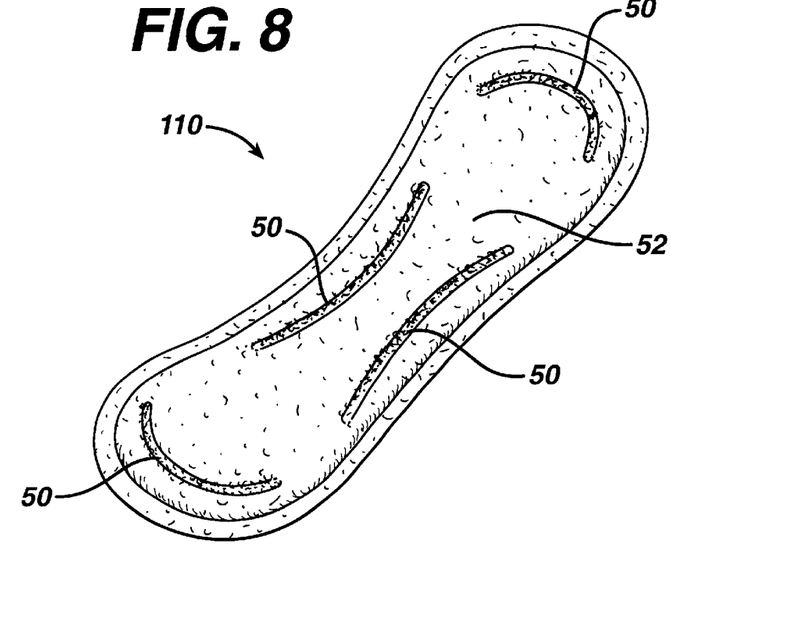
FIG. 8 is a perspective view of a preferred embodiment of an absorbent article of the invention.

FIG. 8 is a perspective view of a preferred embodiment of an absorbent article of the invention, more specifically this absorbent article is a sanitary napkin. This figure illustrates one embodiment of the positioning of densified channels 50 and the resulting centrally located region 52.

Figure 9:
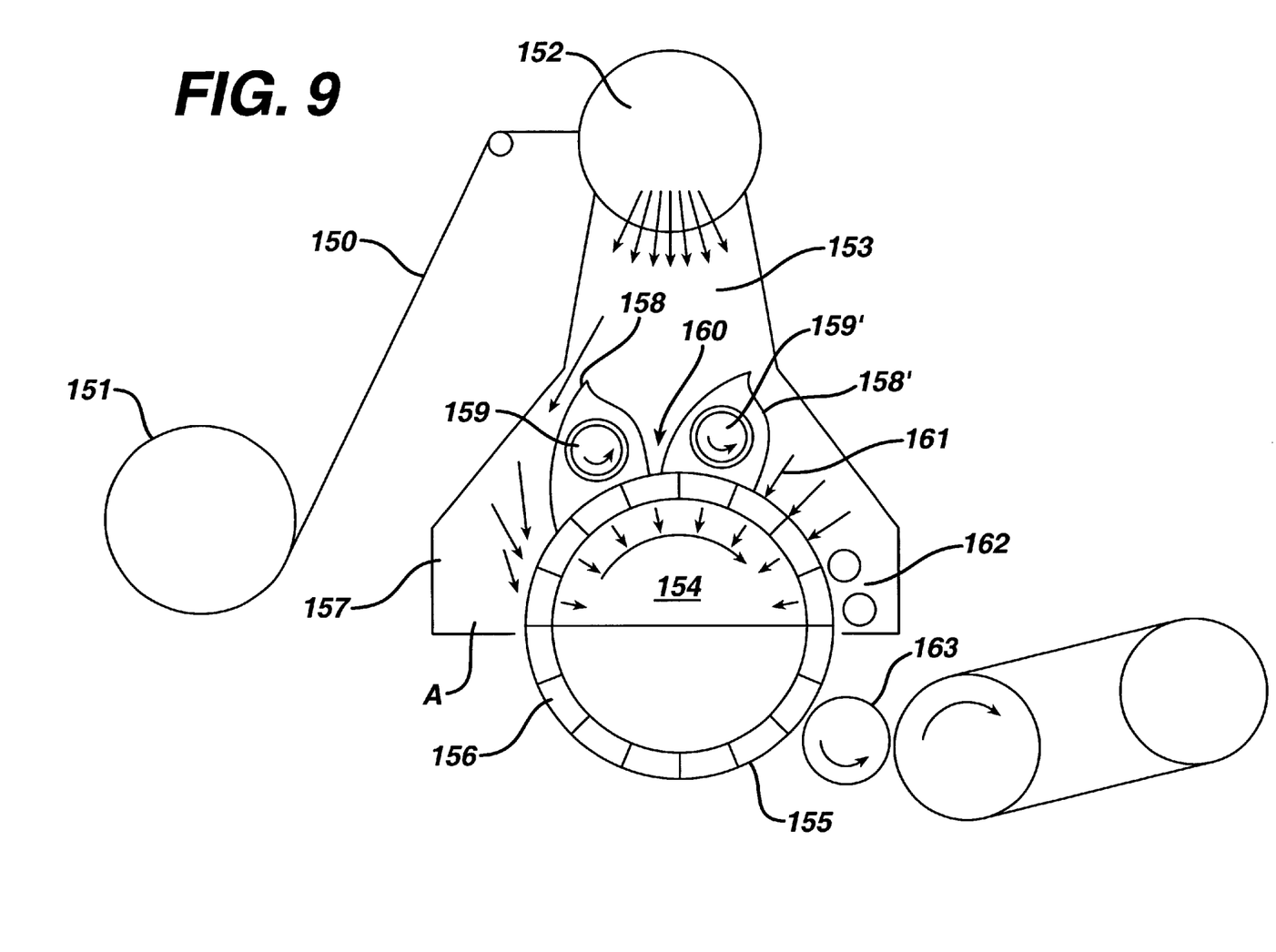
FIG. 9 is a schematic illustration of a preferred apparatus for making the absorbent element of the invention.

A preferred apparatus for making the absorbent structure of the invention is illustrated in FIG. 9. With reference to FIG. 9, the absorbent element of the present invention may be prepared according to the following method. While any of the absorbent fibers as previously discussed may be used to form the absorbent element, for purposes of illustration, wood pulp fibers are used to describe the preferred apparatus. The wood pulp of the absorbent element is supplied in raw material form as a compressed sheet, or pulp board 150, that is wound on a roll. The pulp unwind 151 allows the board to be fed into a pulp mill 152, where a high speed hammer rotor opens the board into substantially individual wood pulp fibers of about 2.5 mm average length, commonly known as pulp fluff or ground wood pulp. Air is pulled through the pulp mill and the adjacent forming chamber 153 by a forming wheel vacuum 154. This air conveys the pulp fluff to a forming wheel 155 and into a mold 156. The molds 156 are cavities in the forming wheel surface spaced around the circumference of the forming wheel 155. The bottom of the molds comprises a porous screen to allow the air to be pulled through the molds, leaving the pulp fluff deposited on the screen.

The molds are mounted on the forming wheel which rotates clockwise. When the molds first enter the forming chamber at position A, they are empty. In the Initial Fiber Deposition Zone 157, 100% pulp fibers are deposited on the bottom of the molds 156. The thickness of pulp deposited in the Initial Fiber Deposition Zone comprises 5% to 25% of the final thickness of the absorbent element, and it acts as a filter to hold the granular superabsorbent polymer powder that will be deposited in the mold. The boundaries of the Initial Fiber Deposition Zone 157 are formed by the left side of the forming chamber 153 and the left side of the seal for the first Particle Application Zone 158.

The first Particle Application Zone 158 comprises a rotary particle applicator valve 159 that dispenses a predetermined amount of particles into the pulp fluff in each mold. The particles are applied in a pattern that is phased with the molds to form the first high absorbency zone. Although the first high absorbency zone shown in this embodiment is generally rectangular, the shape of the first high absorbency zone is not limited to rectangular. Any shape of first high absorbency zone may be used and one of ordinary skill in the art will discern that varying first high absorbency zone shapes may be desirable or even preferable for varying shapes and types of absorbent elements.

The molds then enter an Intermediate Fiber Deposition Zone 160 wherein additional pulp covers the first high absorbency zone.

The second Particle Application Zone 158' is similar to the first Particle Application Zone 158 as it comprises a second rotary particle applicator valve 159' that dispenses a predetermined amount of particles onto the pulp fluff applied in each mold in the Intermediate Fiber Deposition Zone 160. The particles are applied in a pattern that is phased with the molds to form the second high absorbency zone, and in this embodiment, such that the second high absorbency zone is substantially centered in the mold. Preferably, the second high absorbency zone is spaced at least 3 mm inwardly from the peripheral edges of the mold. Most preferably, the second high absorbency zone is spaced at least 7 mm inwardly from the peripheral edges of the mold, and therefore, also at least 7 mm from the peripheral edges of the absorbent element contained therein. Although the second high absorbency zone shown in this embodiment is generally rectangular, the shape of the second high absorbency zone is not limited to rectangular nor is it limited to the same shape as the first high absorbency zone. Any shape of second high absorbency zone may be used and one of ordinary skill in the art will discern that varying second high absorbency zone shapes may be desirable or even preferable for varying shapes and types of absorbent elements.

The molds then enter the Final Fiber Deposition Zone 161 wherein additional pulp covers the second high absorbency zone thereby forming an integral absorbent element. The molds are slightly overfilled with pulp, and two scarfing brushes 162 are used to make the pulp even with the top of the mold. The absorbent elements are then vacuum transferred out of the molds onto the Vacuum Transfer Drum 163, from which they may then be transferred to another forming station for incorporation into absorbent products.

FIGS. 10A, 10B, 11A, 11B, and 12, illustrate the operation of the first and second Rotary Particle Application Valves 159 and 159' in greater detail. Since the first and second Rotary Particle Application Valves 159 and 159' are substantially identical in operation, detailed reference will be made to the first Rotary Particle Application Valve 159 as it operates in the first Particle Application Zone 158. It will be understood that the second Rotary Particle Application Valve 159' in the second Particle Application Zone 158' will function in the same manner as the first Rotary Particle Application Valve 159.

Figure 10A:
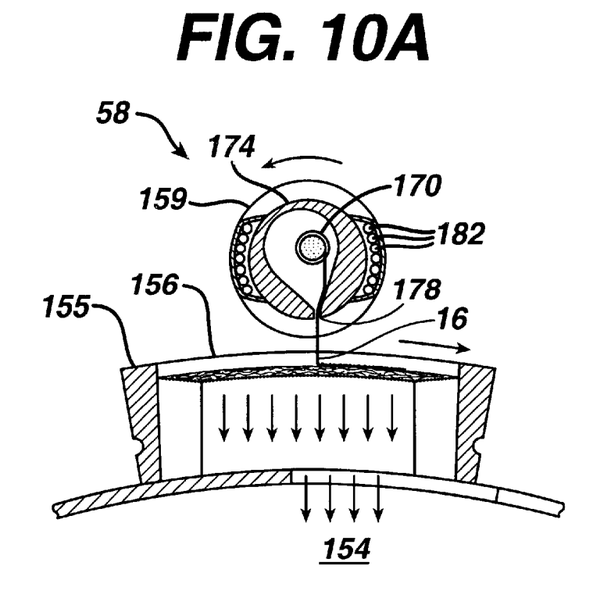
FIG. 10A is a detailed axial view of the particle rotary applicator of the apparatus shown in FIG. 9 in the particle application phase.
Figure 10B:
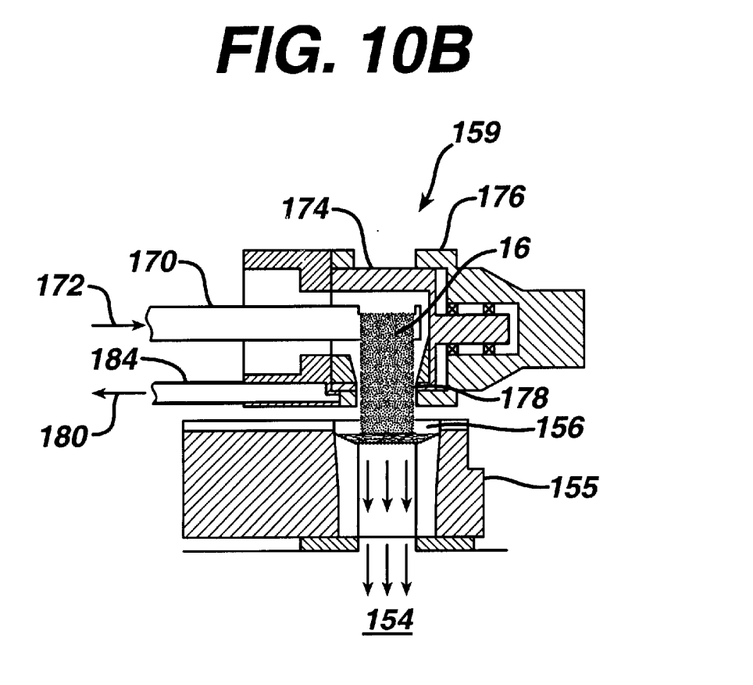
FIG. 10B is a detailed side view of the particle rotary applicator of the apparatus shown in FIG. 9 in the particle application phase.

FIGS. 10A and 10B show an axial view and a side view respectively of first Rotary Particle Application Valve 159 in the particle application phase. In order to achieve a precise pattern of particles on each mold 156, first Rotary Particle Application Valve 159 is used as a means to start and stop the flow of particles to the molds 156. Particles are delivered to the first Rotary Particle Application Valve 159, in the first Particle Application Zone 158. Preferably, the particles are delivered via a first gravimetric feeder, such as a loss-in-weight (LIW) screw feeder 170 to accurately control the particle weight applied to each mold 156. The first particle supply source 172 is located outside of the first Particle Application Zone. The discharge end of the screw feeder 170 is located within a stationary funnel 174 of the first Rotary Particle Application Valve. The stationary funnel is housed within the rotor 176 of the first Rotary Particle Application Valve. The rotor 176 comprises at least one rotor slot opening 178. The widths of the stationary funnel 174, the rotor slot opening 178, and the discharge end of the screw feeder 170 are matched to the width of the desired pattern of particles to be formed on each mold, which determines the shape of the first high absorbency zone. As the rotor 176 turns, and the rotor slot opening 178 aligns with the discharge end of the screw feeder 170, the superabsorbent polymer particles 16 contained in the stationary funnel drop by gravity onto the mold 156. The forming wheel vacuum 154 assists with the drawing of the particles downward onto the mold 156. Preferably, a portion of the screen bottom of each mold 156 is also masked such that an opening remains having the desired pattern shape. This selective masking of the pulp molds enhances the accurate and precise placement of the particles within the pulp mold. The length of the rotor slot 178 dictates the length of the pattern of particle forming the first high absorbency zone 8 of the absorbent element 1.

Figure 11A:
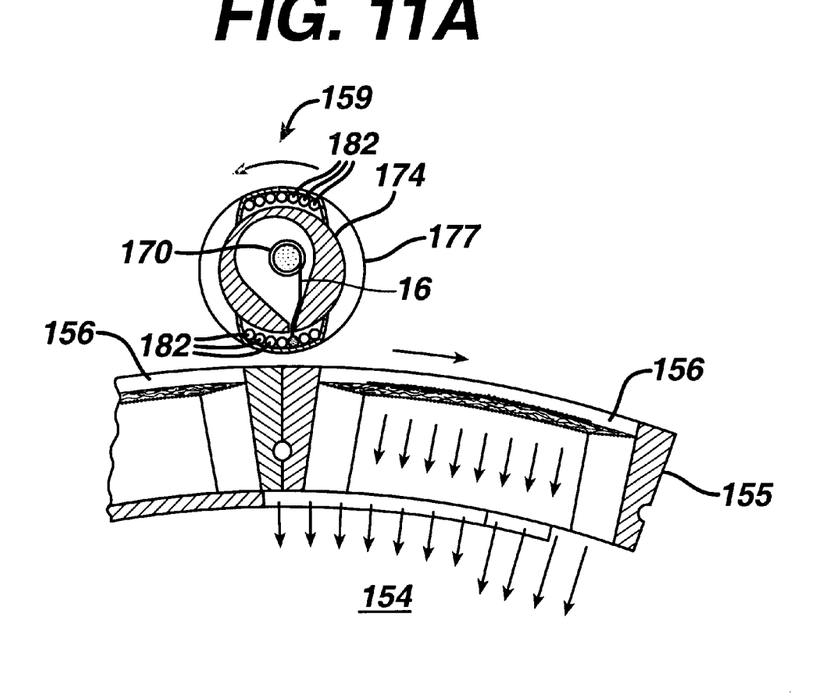
FIG. 11A is a detailed axial view of the particle rotary applicator of the apparatus shown in FIG. 9 in the recycle phase.
Figure 11B:
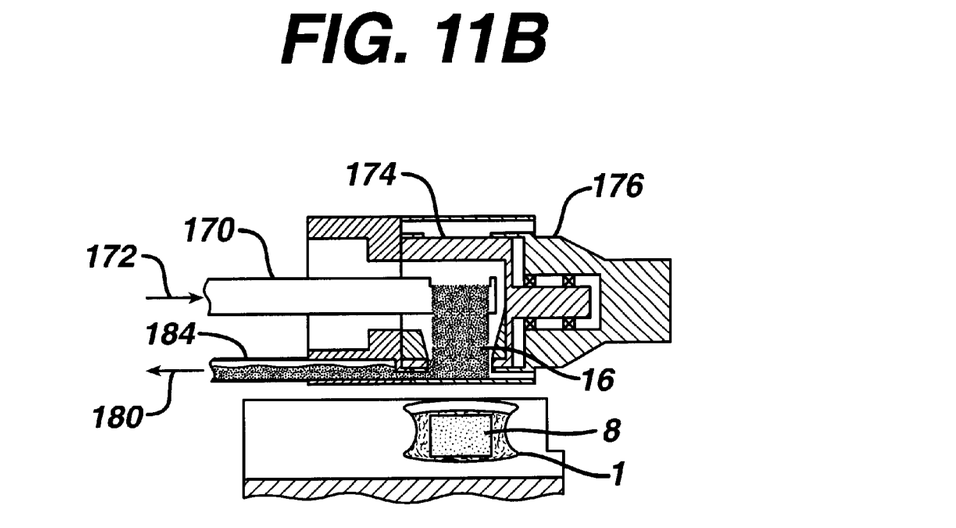
FIG. 11B is a detailed side view of the particle rotary applicator of the apparatus shown in FIG. 9 in the recycle phase.
Figure 12:
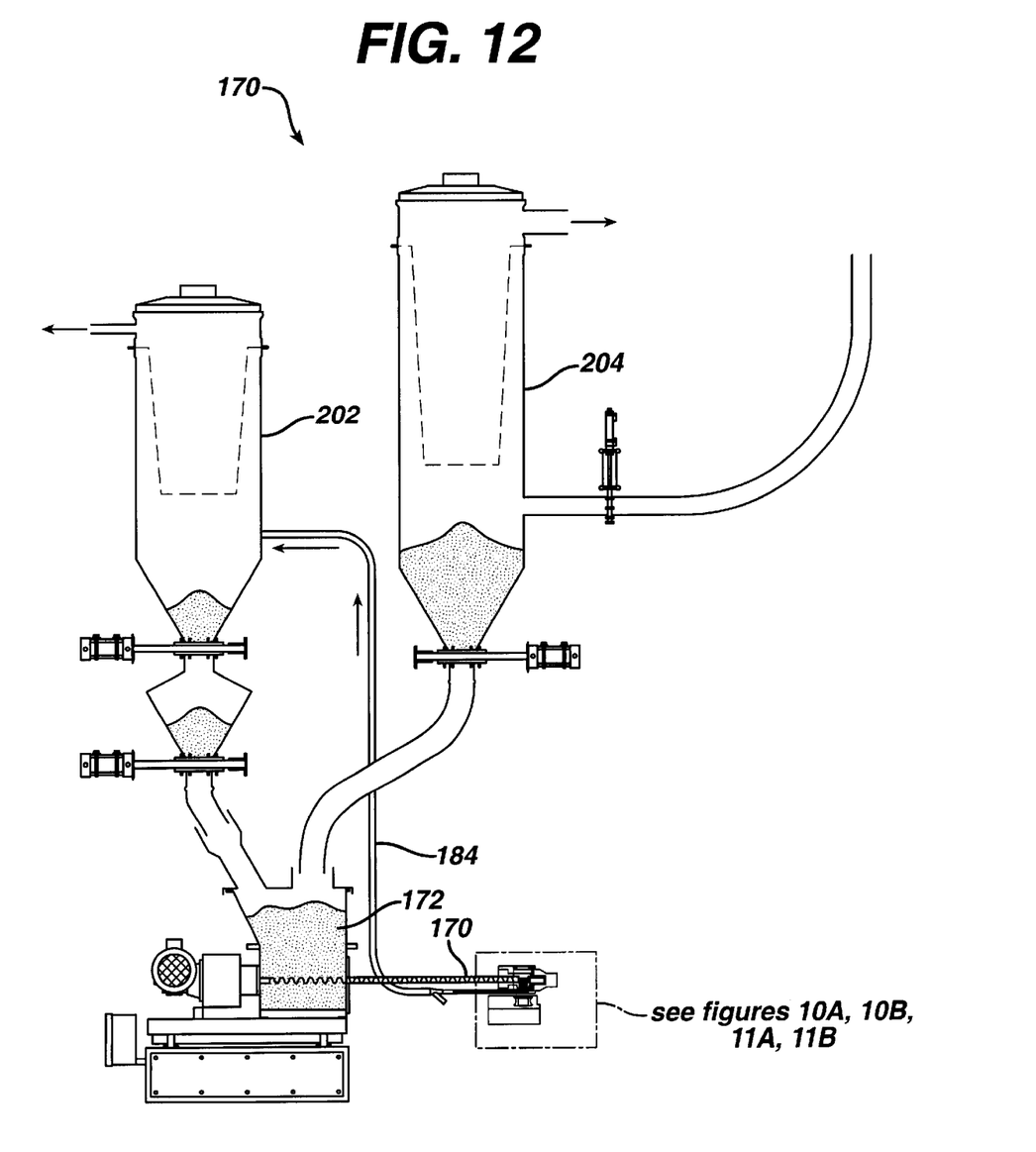
FIG. 12 is a detailed view of the gravimetric feeder and powder receivers to supply the particle rotary applicator of the apparatus shown in FIG. 9.

FIGS. 11A and 11B show an axial view and a side view respectively of the first Rotary Particle Application Valve 159 in the recycle phase. In FIGS. 11A and 11B, the forming wheel 155 is shown in a position such that the first Rotary Particle Application Valve 159 is located over a portion of the wheel between two molds 156. It is desired to prevent the deposition of particles over this portion of the wheel, since any particles dispensed in this position are essentially wasted and serve only to contaminate the area surrounding the apparatus. The recycle phase shown in FIGS. 11A and 11B prevents the problems associated with unwanted disposition of particles by recycling the particles. When the first Rotary Particle Application Valve 159 is in the recycle phase as shown, the position of the rotor 176 under the stationary funnel 174 prevents the passage of particles; i.e., the rotor slot 178 is in a closed position. Particles exiting the first screw feeder 170 hit the inside diameter of the rotor. A rotor vacuum port 180 in the side of the rotor opens to the rotor inside diameter through a series of recycle holes 182 in the rotor and pulls the particles out of the rotor and into a recycling tube 184. As shown in FIG. 12, the particles are then conveyed by air through the recycling tube 184 to a recycle receiver 202 that will eventually provide the particles back to the first screw feeder 170 for reuse. Also shown in FIG. 12 is a detailed view of the first particle supply source 172, including both the virgin supply reservoir 204 and the recycle receiver 202.

Likewise, the second Rotary Particle Applicator Valve 159' in the second particle Application Zone 158' functions similarly. Third and fourth and more rotary particle applicator valves may also be added in a similar manner to produce absorbent elements with more than two high absorbency zones separated from one another throughout the thickness of the absorbent element.

The specification and embodiments above are presented to aid in the complete and non-limiting understanding of the invention disclosed herein. Since many variations and embodiments of the invention can be made without departing from its spirit and scope, the invention resides in the claims hereinafter appended.

We claim:

1. An absorbent structure comprising an integral absorbent element having no identifiable laminate layers and having an upper surface and a lower surface defining therebetween an absorbent element thickness, the absorbent element further comprising a first high absorbency zone and a second high absorbency zone, the first high absorbency zone being separated from the second high absorbency zone by a portion of the absorbent element thickness, each of the first and second high absorbency zones comprising a mixture of absorbent fibers and superabsorbent polymer particles, wherein the portion of the absorbent element thickness is substantially free of superabsorbent polymer particles.

2. The absorbent structure of claim 1 wherein the superabsorbent polymer particles are uniformly mixed with absorbent fibers within at least one of the first and second high absorbency zones.

3. The absorbent structure of claim 1 wherein the superabsorbent polymer particles are present in each high absorbency zone at a loading of between 30 and 55 grams per square meter.

4. The absorbent structure of claim 1 wherein the absorbent element upper surface is substantially free of superabsorbent polymer particles.

5. The absorbent structure of claim 1 wherein the absorbent fibers comprise wood pulp fibers.

6. The absorbent structure of claim 1 having at least two spaced apart densified channels and wherein at least one of the first and second high absorbency zones is confined between the at least two densified channels.

7. The absorbent structure of claim 1 wherein the first high absorbency zone comprises about 15% of the absorbent element thickness, the first high absorbency zone being located within an upper 25% of the absorbent element thickness.

8. The absorbent structure of claim 1 wherein the first high absorbency zone comprises about 10% of the absorbent element thickness, the first high absorbency zone being located within an upper 20% of the absorbent element thickness.

9. The absorbent structure of claim 1 wherein the first high absorbency zone comprises first superabsorbent polymer particles and the second high absorbency zone comprises second superabsorbent polymer particles and wherein the first high superabsorbent polymer particles are different from the second superabsorbent polymer particles.

10. The absorbent structure of claim 1 wherein the first high absorbency zone comprises a first percentage of superabsorbent polymer particles and the second high absorbency zone comprises a second percentage of superabsorbent polymer particles and wherein the first percentage is different than the second percentage.

11. The absorbent structure of claim 1 wherein the absorbent element further comprises absorbent materials selected from the group consisting of binders, odor-controlling particles, perfumes, ethylene vinyl acetate based latex binders, adhesives, thermally fusible fibers, and bicomponent fibers.

12. The absorbent structure of claim 1 wherein the absorbent element further comprises nonabsorbent materials selected from the group consisting of nonabsorbent fibers, binders, odor controlling particles, perfumes, ethylene vinyl acetate based latex binders, adhesives, thermally fusible fibers, and bicomponent fibers.

13. The absorbent structure of claim 1 further comprising a third high absorbency zone, wherein the first high absorbency zone is separated from the second high absorbency zone by a first portion of the absorbent element thickness and the second high absorbency zone is separated from the third high absorbency zone by a second portion of the absorbent element thickness, the first and second portions of the absorbent element thickness are substantially free of superabsorbent polymer particles.

14. The absorbent structure of claim 1 further comprising two or more additional absorbency zones, wherein each additional zone is separated from a subjacent absorbency zone by a portion of the absorbent element thickness, which portion is substantially free of superabsorbent polymer particles.

15. An absorbent article adapted to be worn in a crotch portion of a user's undergarment, the article comprising:

a liquid permeable body-facing layer;

a liquid impermeable barrier layer; and an absorbent structure comprising an integral absorbent element having no identifiable laminant layers and having an upper surface and a lower surface defining therebetween an absorbent element thickness, the absorbent element further comprising a first high absorbency zone and a second high absorbency zone, the first high absorbency zone being separated from the second high absorbency zone by a portion of the absorbent element thickness, each of the first and second high absorbency zones comprising a mixture of absorbent fibers and superabsorbent polymer particles, wherein the portion of the absorbent element thickness is substantially free of superabsorbent polymer particles.

16. The absorbent article of claim 15 wherein the superabsorbent polymer particles are uniformly mixed with absorbent fibers within at least one of the first and second high absorbency zones.

17. The absorbent article of claim 15 wherein the absorbent element upper surface is substantially free of superabsorbent polymer particles.

18. The absorbent article of claim 15 wherein the absorbent fibers comprise wood pulp fibers.

19. The absorbent article of claim 15 wherein the superabsorbent polymer particles are present in each high absorbency zone at a loading of between about 30 and 55 grams per square meter.

20. The absorbent article of claim 15 wherein the superabsorbent polymer comprises a crosslinked polyacrylate.

21. The absorbent article of claim 15 wherein the first high absorbency zone has a first zone thickness comprising about 15% of the absorbent element thickness, the first high absorbency zone being located within an upper 25% of the absorbent element thickness.

22. The absorbent article of claim 15 wherein the first high absorbency zone has a first zone thickness comprising about 10% of the absorbent element thickness, the first high absorbency zone being located within an upper 20% of the absorbent element thickness.

* * * * *